US008048860B2

(12) United States Patent
Yang et al.

(10) Patent No.: US 8,048,860 B2
(45) Date of Patent: Nov. 1, 2011

(54) **BUTANOL EXTRACT OF *BIDENS PILOSA***

(75) Inventors: Wen-Chin Yang, Taichung County (TW); Shu-Lin Chang, Hsin-Chu (TW); Lee-Tian Chang, Taichung (TW); Yi-Ming Chiang, Taipei County (TW); Lie-Fen Shyur, Nankang (TW)

(73) Assignee: Academia Sinica, Taipei (TW)

( * ) Notice: Subject to any disclaimer, the term of this patent is extended or adjusted under 35 U.S.C. 154(b) by 382 days.

(21) Appl. No.: 12/263,896

(22) Filed: Nov. 3, 2008

(65) Prior Publication Data

US 2009/0062216 A1 Mar. 5, 2009

Related U.S. Application Data

(62) Division of application No. 11/219,503, filed on Sep. 2, 2005, now abandoned.

(51) Int. Cl.
*A61K 31/7032* (2006.01)
*C07G 3/00* (2006.01)
*C07H 15/10* (2006.01)

(52) U.S. Cl. .......................................... 514/25; 536/4.1

(58) Field of Classification Search ........................ None
See application file for complete search history.

(56) References Cited

U.S. PATENT DOCUMENTS

2007/0053998 A1 3/2007 Yang et al.
2010/0204166 A1* 8/2010 Yang ................................ 514/25

FOREIGN PATENT DOCUMENTS

| JP | 2002205954 | 7/2002 |
| JP | 2004083463 | 3/2004 |
| WO | WO 95/23214 | 8/1995 |

OTHER PUBLICATIONS

Machine translation of JP2004-083463, published Mar. 2004, downloaded from www.ipdl.inpit.go.jp.*
Van den Berg et al., "Amelioration of established murine collagen-induced arthritis with anti-IL-1 treatment" Clin Exp Immunol. (1994) vol. 95, pp. 237-243.*
"Tolbutamide", downloaded from PubMed Health at http://www.ncbi.nlm.nih.gov/pubmedhealth/PMH0000692/, revised Jul. 1, 2010.*
Christiansen et al., "Discovery of Potent and Selective Agonists for the Free Fatty Acid Receptor 1 (FRFA1/GPR 40), a Potent Target for the Treatment of Type II Diabetes," J. Med. Chem. 61: 7061-7064 (2008).
Ren et al., "Synthesis and Structure-Activity Relationship Study of Antidiabetic Penta-O-Gallyol-D-Dlucopyranose and its Analogurd," J. Med. Chem. 49:2829-2837 (2006).
Neogi et al., "Synthesis and Structure-Activity Relationship Studies of Cinnamic Acid-Based Novel Thiazolidinedione Antihyperglycemic Agents," Bioorganic & Medicinal Chemistry, 11:4059-4067 (2003).
Kim et al., "Design, Synthesis and Structure-Activity Relationship of Carbamate-Tethered Aryl Propanoic Acids as Novel PPAR Alpha/Gamme Dual Agonists," Bioorganic & Medicinal Chemistry Letters, 17:3595-3598 (2007).
Miura et al., "Hypoglycemic Activity and Structure-Activity Relationship of Iridoidal Glycosides," Bio Pharm. Bull. 19(1): 160-161 (1996).
Bell, "Type 2 Diabetes Mellitus: What is the Optimal Treatment Regimen?" The American Journal of Medicine vol. 116: 23S-29S (2004).
Verspohl, E.J., "Recommended Testing in Diabetes Research," Planta Med. 61:581-590 (2002).
Wicksteed et al., "Glucose-Induced Translation Control of ProinsulinBiosynthesis is Proportional to Preproinsulin mRNA Levels in Islet B-Cells But Not Regulated via a Positive Feedback of Secreted Insulin," The Journal of Biological Chemistry, vol. 278, 43:42080-42090 (2003).
Henquin, "Perspectives in Diabetes Triggering and Amplifying Pathways of Regulation of Insulin Secretion by Glucose," Diabetes 49:1751-1760.
Leibiger et al., "Exocytosis of Insulin Promotes Insulin Gene Transcription via the Insulin Receptor/PI-3 Kinase/p70 s6 kinase and CaM Kinase Pathways,"Molecular Cell, 1:933-938 (1998).
Oubré et al., "From Plant to Patient: An Ethnomedical Approach to the Identification of New Drugs for the Treatment of NIDDM" Daibetologia, 40:614-617 (1997).
Habeck, M., "Diabetes Treatments Get Sweet Help from Nature," Nature Medicine, 9:1228 (2003).
Alarcon-Aguilar et al., "Investigation on the hypoglacaemic Effects of Extracts of Four Mexican Medicinal Plants in Normal and Alloxan-diabetic Mice," Phytotherapy Research, 16:383-386 (2002).
Krettli et al., "The Search for New Antimalarial Drugs from Plants Used to Treat Fever and Malaria or Plants Randomly (sic) Selected: A Review," Mem Inst Oswaldo Cruz, 96(8): 1033-1042 (2001).

(Continued)

*Primary Examiner* — Eric S Olson
(74) *Attorney, Agent, or Firm* — Occhiuti Rohlicek & Tsao LLP

(57) ABSTRACT

A method of treating a Th1-mediated disorder includes administering to a subject in need of the treatment an effective amount of a compound of the formula I:

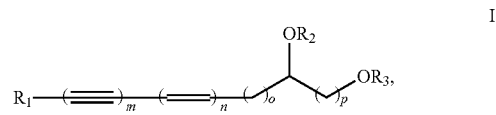

wherein $R_1$ is H, alkyl, aryl, or cyclyl; $R_2$ is pyranose; $R_3$ is H or alkyl; m is 2, 3, 4, 5, or 6; n is 0, 1, 2, or 3; o is 0, 1, 2, 3, 4; p is 1, 2, 3, or 4; and the Th1-mediated disorder is non-obese diabetes, Crohn's colitis, autoimmune hemolytic anemia, rheumatoid arthritis, autoimmune encephalitis, multiple sclerosis, or autoimmune myocarditis. Also disclosed is a pharmaceutical composition including a compound of formula I above and a pharmaceutically acceptable carrier.

17 Claims, No Drawings

OTHER PUBLICATIONS

Geissberger et al., "Constituents of *Bidens pilosa* :Do the components found so far explain the use of this plant in traditional medicine?" Acta Tropica 48:251-261 (1991).

Jager et al., "Screening of Zulu Medicinal Plants for Prostaglandin-Synthesis Inhibitors," Journal of Ethnopharmacology 52:95-100 (1996).

Rabe et al., "Antibacterial Activity of South African Plants Used for Medicinal Purposes," Journal of Enthopharmacology, 56:81-87 (1997).

Alvarez et al., "Bioactive Polyacetylenes from *Bidens pilosa*," Planta Medica 62:355-357, (1996).

Abbas et al., "T Lymphocytes and the Initiation of Cell-Mediated Immune Reactions," Cellular and Molecular Immunology, Section III 262-277.

Abbas et al., "Functional Diversity of Helper T Lymphocytes," Nature 383:787-792, (1996).

Farnsworth, "The Role of Medicinal Plants in Drug Development," Natural Products and Drug Development, Alfred Benzon Symposium 20, (1984).

Pereira et al., "Immunosuppressive and Anti-Inflammatory Effects of Methanolic Extract and Polyacetylene Isolated from *Bidens pilosa* L. Immunosuppressive and Anti-Inflammatory Effects of Methanolic Extract and Polyacetylene Isolated from *Bidens pilosa* L." Immunopharmacology 43:31-37, (1999).

Brandao et al., "Antimalarial activity of Extracts and Fractions from *Bidens pilosa* and Other *Bidens* Species (Asteraceae) Correlated with the Presence of Acetylene and Flavonoid Compounds," Journal of Ethnopharmacology 57:131-138, (1997).

Chih et al., "Anti-Inflammatory Activity of Taiwan Folk Medicine Ham-Hong-Chho in Rats," American Journal of Chinese Medicine, vol. XXIII, Nos. 3-4, pp. 273-278, (1995).

Rucker et al., "Acetylenic Glucosides from *Microglossa pyrifolia*" Planta Medica 58:266-269, (1992).

Ubillas et al., "Antihyperglycemic Acetylenic Glucosides from *Bidens pilosa*" Planta Medica 66:82-83, (2000).

Zhao et al., "A New Chalcone Glycoside from *Bidens pilosa*".

Ubillas et al., Planta Med. 66:82-53 (2000).

Chang et al., "Polyacetylenic Compounds and Butanol Fraction from *Bidens pilosa* can Modulate the Differentiation of Helper T Cells and Prevent Autoimmune Diabetes in Non-Obese Diabetic Mice," Planta Med., 70: 1045-1051 (2004).

Chang et al., "The distinct effectsd of a butanol fraction of *Bidens pilosa* plant extract on the development of TH1-mediated diabetes and Th2-mediated airway inflammation in mice," Journal of Biomedical Science, 12:79-89 (2005).

Chiang et al., "Cytopiloyne, a novel polyacetylenic glucoside from *Bidens pilosa*, functions as a T helper cell modulator," Journal of Ethnopharmacology, 110:532-538 (2007).

Wu et al., "Polyacetylese Function as Anti-Angiogenic Agents," Pharmaceutical Research, vol. 2: 2112-2119 (Nov. 2004).

McClenaghan et al., "Physiological and Pharmacological Regulation of Insulin Release: Insights Offered Through Exploitation of Insulin-Secreting Cell Lines," Diabetes, Obesity and Metabolism, 137-150 (1999).

Vinik et al., "Prevention of the Complications of Diabetes," American Jounral of Managed Care, vol. 9, S63-S80 (2003).

Boyle et al., "Estimating Prevalence of Type 1 and Type 2 Diabetes in a Population of African Americans with Diabetes Mellitus," American Journal of Epidemiology, vol. 149; 55-63 (1999).

Melloul et al, "Regulation of Insulin Gene Transcription," Diabetologica, 45:309-326 (2002).

Del Prato et al., "The Importance of First-Phase Insulin Secretion: Implications for the Therapy of Type 2 Diabetes Mellitus," Diabetes/Metabolism Research and Reviews, 17:164-174 (2001).

Attele et al., "Antidiabetic Effects of Panax ginseng Berry Extract and the Identification of an Effective Component," Diabetes, vol. 51, 1851-1858 Jun. 2002.

Ravid et al., "Cardiovascular Protection in Patients with Type 2 Diabetes Mellitus: Considerations about the Tightness of Blood Pressure Control and the Choice of Treatment," European Journal of Internal Medicine, 16:154-159 (2005).

Henquin, "Perspectives in Diabetes Triggering and Amplifying Pathways of Regulation of Insulin Secretion by Glucose," Diabetes 49:1751-1760, ( 2000).

Geissberger et al., "Constituents of *Bidens pilosa* :Do the components found so far explain the use of this plant in traditional medicine?" Acta Tropica 48:251-261 (1991).

Abbas et al., "T Lymphocytes and the Initiation of Cell-Mediated Immune Reactions," Cellular and Molecular Immunology, Section III 262-277 (1994).

Zhao et al., "A New Chalcone Glycoside from *Bidens pilosa*", (2004).

* cited by examiner

BUTANOL EXTRACT OF *BIDENS PILOSA*

RELATED APPLICATION

This application is a divisional application of and claims priority to U.S. patent application Ser. No. 11/219,503, filed Sep. 2, 2005, the contents of which are herein incorporated by reference.

BACKGROUND

T cells, a class of lymphocytes developed in the thymus, are responsible for cell- and antibody-mediated immunity. Two major classes of T cells perform very different functions. $CD8^+$ cytotoxic T cells kill infected cells or eliminated microorganisms, and $CD4^+$ helper T cells help activate responses of other white cells, mainly by secreting a variety of local mediators lymphokines, interleukins, or cytokines.

There are two subsets of helper T cells, i.e., Th1 and Th2 cells, which function differently. Th1 cells mediate cellular immunity. They are related to rheumatoid arthritis, non-obese diabetes, and colitis. Th2 cells mediate humoral immunity. They are related to humoral immune response, asthma, inflammation, and allergy. Both Th1 and Th2 cells are derived from naive helper T cells (Th0).

SUMMARY

This invention is based on a surprising finding that a butanol extract from *Bidens pilosa* and three compounds isolated from this plant effectively inhibit Th1 cell differentiation and promote Th2 cell differentiation.

Thus, one aspect of this invention is a *Bidens pilosa* extract prepared by a method including (1) stirring a pulverized *Bidens pilosa* plant in water (e.g., boiling water) to form a suspension, (2) collecting an aqueous solution from the suspension, and (3) extracting the aqueous solution with butanol to provide the extract.

Also within the scope of this invention are compounds of formula I shown below:

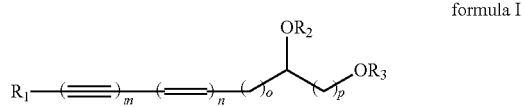

formula I wherein $R_1$ is H, alkyl, aryl, or cyclyl; $R_2$ is pyranose; $R_3$ is H or alkyl; m is 2, 3, or 4; n is 0; o is 0, 1, 2, 3, 4; and p is 1, 2, 3, or 4. These compounds are either present in the above-described extract or analogues thereof.

Referring to formula I, $R_1$ can be methyl, $R_2$ can be β-glucopyranose, $R_3$ can be H, m can be 4, o can be 2, and p can be 1.

Yet another aspect of this invention is a method of inhibiting Th1 cell differentiation or promoting Th2 cell differentiation. The method includes administering to a subject an effective amount of the above-described *Bidens pilosa* extract or a compound of formula II:

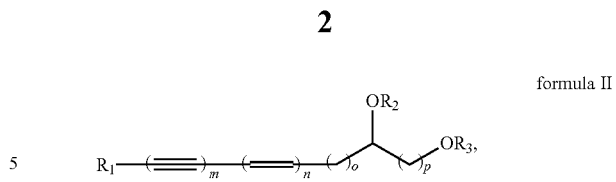

formula II wherein $R_1$ is H, alkyl, aryl, or cyclyl; $R_2$ is pyranose; $R_3$ is H or alkyl; m is 2, 3, 4, 5, or 6; n is 0, 1, 2, or 3; o is 0, 1, 2, 3, 4; and p is 1, 2, 3, or 4.

Referring to formula $T_1$, $R_1$ can be methyl, $R_2$ can be β-glucopyranose, and $R_3$ can be H.

Set forth below are three exemplary unsaturated compounds that can be used to practice this method:

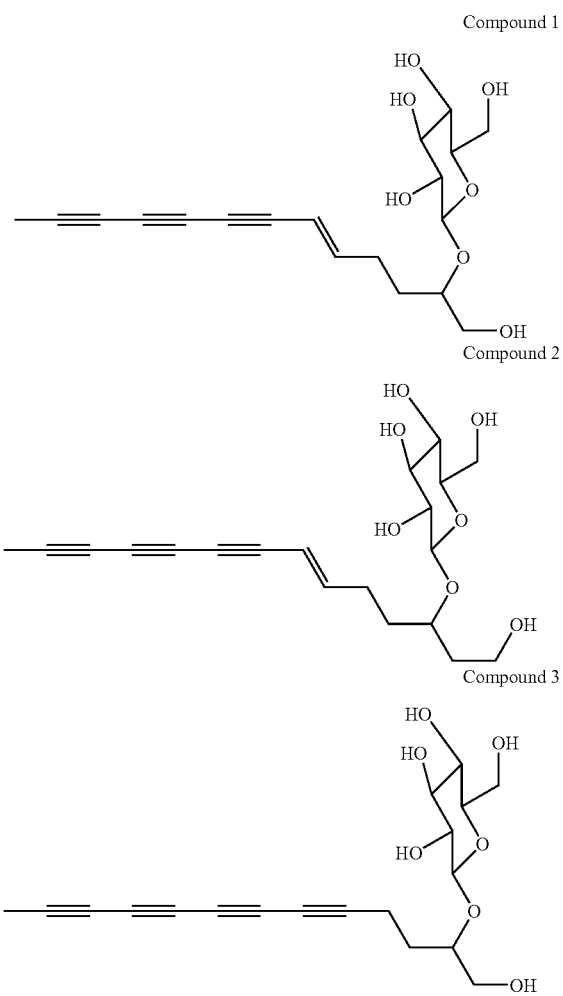

Also within the scope of this invention is a composition containing the above-described *Bidens pilosa* extract or a compound of formula II and a pharmaceutically acceptable carrier, as well as use of the composition for the manufacture of a medicament for inhibiting Th1 cell differentiation, promoting Th2 cell differentiation, or treating Th1 or Th2-mediated disorders.

The details of one or more embodiments of the invention are set forth in the description below. Other features, objects, and advantages of the invention will be apparent from the description, and from the claims.

DETAILED DESCRIPTION

This invention relates to a *Bidens pilosa* extract and its use in inhibiting Th1 differentiation from Th0 and promoting Th2 differentiation from Th0.

The extract can be prepared from *Biodens pilosa* plant by first extracting the plant with water and then extract the water solution with butanol. A detailed procedure of preparing such an extract is provided in an example below. The *Bidens pilosa* plant is a tropical weed used widely in herbal medicine. Its cultivation, growth, taxonomy, and agriculture practice are well known in the art. See, e.g., Duke. J. A. et al. *Medicinal Plants of China*, Reference Publications, Inc. 1985.

This invention also relates to the compounds of formula I or formula II described above. These compounds can be either isolated from the above-described extract or synthesized by conventional methods. The isolation can be conducted by extraction, thin layer chromatography, high pressure liquid chromatography, and/or other suitable techniques. The synthesis includes total synthesis from smaller molecules and modification of functional groups on analogous compounds.

The chemicals used in the synthesis may include, for example, solvents, reagents, catalysts, protecting group and deprotecting group reagents. In addition, various synthetic steps may be performed in an alternate sequence to give the desired compounds. Synthetic chemistry transformations and protecting group methodologies (protection and deprotection) useful in synthesizing applicable fused pyrazolyl compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The above-described extract and compounds inhibit Th1 cell differentiation and promote Th2 differentiation. Thus, this invention relates to methods of inhibiting Th1 cell differentiation, promoting Th2 differentiation, or treating a Th1-mediated disorder or a Th2-mediated disorder by administering to a subject in need thereof an effective amount of the active extract or one or more of the active compounds. The term "an effective amount" refers to the amount of the active substance which is required to confer one of the above-described effects in the subject. Effective amounts may vary, as recognized by those skilled in the art, depending on route of administration, excipient usage, and the possibility of co-usage with other agents. The term "treating" refers to administering such an active substance to a subject that has a Th1-mediated disorder or a Th2-mediated disorder, or has a symptom of the disorder, or has a predisposition toward the disorder, with the purpose to cure, heal, alleviate, relieve, alter, remedy, ameliorate, improve, or affect the disorder, the symptoms of the disorder, or the predisposition toward the disorder. The terms "Th1-mediated disorder" and "Th2-mediated disorder" refers to disorders which can be treated by mediating Th1 cell differentiation and Th2 differentiation, respectively. Examples of Th1-mediated disorders include, but are not limited to, non-obese diabetes, Crohn's colitis, autoimmune hemolytic anemia, rheumatoid arthritis, autoimmune encephalitis, multiple sclerosis, or autoimmune myocarditis.

To practice one of the above-described methods, one administers to a subject in need thereof orally, rectally, parenterally, by inhalation spray, or via an implanted reservoir a composition that contains either the extract or one or more of the compounds. The composition may also contain a pharmaceutically acceptable carrier. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% almond and about 70% white soft paraffin by weight.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active compounds. Examples of other carriers include colloidal silicon dioxide, magnesium stearate, cellulose, sodium lauryl sulfate, and D&C Yellow # 10.

A suitable in vitro assay can be used to preliminarily evaluate the efficacy of the above-described extract or one or more of the above-described compounds in inhibiting Th1 differentiation or promoting Th2 differentiation. The active substance can further be examined for its efficacy in treating Th1-mediated disorder or an Th2-mediated disorder by in vivo assays. For example, the active substance can be administered to an animal (e.g., a mouse model) having a Th1 or Th2-mediated disorder and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever. All of the publications, including patents, cited herein are hereby incorporated by reference in their entirety.

EXAMPLE 1

*Bidens pilosa* was collected on the campus of Academia Sinica, Taiwan (voucher specimen No. 0211943, deposited at the Herbarium of the Department of Botany, National Taiwan University, Taipei, Taiwan). Approximately 10 kg of crushed plant in 40 L of water was refluxed for 2 h. The residue was again refluxed in 25 L of water for 2 h. The two aqueous solutions were combined and then evaporated in vacuo to yield a residue, which was subsequently suspended in 1.0 L of water and extracted with 1.0 L of n-butanol 3 times. The butanol fraction was evaporated on a vacuum rotary evaporator under reduced pressure to remove the solvent and then lyophilized to provide 37.7 g of a crude product (BPB).

BPB (5.0 g) was further purified by a RP-18 silica gel column (100 g) with a MeOH/$H_2O$ gradient solvent system to give 4 fractions: BPB1 (10% MeOH), BPB2 (40% MeOH), BPB3 (100% MeOH), and BPB4 (100% MeOH). BPB3 (0.621 g) was further isolated by semi-preparative HPLC having a RP-18 column (Phenomenex Luna 5m C18 (2), 250 mm×10 mm) and a UV 254 nm detector using a MeOH/$H_2O$ gradient at a flow rate of 4.0 ml/min. Two fractions were collected at the retention time of 18.7 and 20.5 min, respectively. The HPLC gradient was MeOH (solvent B) in $H_2O$ (solvent A): 40 to 70% from 0 to 30 min, 70 to 100% from 30 to 32 min, maintained at 100% from 32 to 37 min, 100 to 40% from 37 to 40 min. The above percentages refer to those of solvent B in the solvent gradient. Further HPLC purification of the first fraction with 35% MeCN/$H_2O$ afforded pure Compound 1 (18.5 mg). Further HPLC purification of the second fraction with 35% MeCN/$H_2O$ afforded Compound 2 (22.6 mg) and Compound 3 (12.3 mg).

$^1$H NMR ($CD_3OD$) of Compound 3: δ 1.78 (2H, q, 6.8), 1.98 (3H, s), 2.58 (2H, t, 6.8), 3.19 (1H, dd, 9.1, 7.8), 3.30 (2H, m), 3.34 (1H, m), 3.59 (2H, m), 3.65 (1H, dd, 12.0, 6.5), 3.75 (1H, p, 6.8), 3.85 (1H, dd, 12.0, 1.7), 4.32 (1H, d, 7.8).

$^{13}$C NMR ($CD_3OD$) of Compound 3: δ 3.8 (q), 16.1 (t), 31.4 (t), 60.0 (s), 60.9 (s), 61.8 (s), 62.4 (s), 62.6 (t), 64.9 (s), 65.8 (t), 66.2 (s), 71.5 (d), 75.2 (d), 77.9 (s), 77.9 (d), 77.9 (d), 81.6 (s), 81.6 (d), 104.8 (d).

EXAMPLE 2

In Vitro Assay:

Human umbilical cord blood CD4$^+$ Th0 cells, provided by Taipei Medical University Hospital, were purified with a MACS column (Miltenyi, Calif.) and grown in RPMI 1640 medium supplemented with 10% FCS, penicillin (100 U/ml), streptomycin (100 μg/ml), 2-ME (10 μM), sodium pyruvate (1 mM), and glutamate (292 μg/ml). The Th0 cells (0.5×10$^6$/ml) were incubated in RPMI medium containing phytohemagglutinin (2 μg/ml), IL-12 (2 ng/ml), and anti-IL-4 antibody (200 ng/ml) (Th1 condition), or in RPMI medium containing phytohemagglutinin (2 μg/ml), IL-4 (10 ng/ml) and anti-IL-12 antibody (2 μg/ml) (Th2 condition). IL-2 (5 ng/ml) was added 48 h later. The T cells were treated with BPB, Compound 1, Compound 2, or Compound 3 for 24 h on day 5 under the Th1 condition or Th2 condition. For cytokine intracellular staining, the T cells were treated with phorbol 12 myristate 13-acetate (50 nM) plus ionomycin (0.5 ug/ml) for 4 hr, followed by Golgiplug (BD Biosciences, NJ) for 2 h. Then, the cell numbers were measured by the fluorescence activated cell sorter analysis.

The results show that each of BPB and the 3 compounds inhibited differentiation of Th0 cells to Th1 cells and promoted differentiation of Th0 to Th2 cells.

In Vivo Assay:

Female mice susceptible to non-obese diabetes were purchased from Jackson Laboratory (Bar Harbor, Me.). They were divided into three groups. The first group (3 mice), the second group (6 mice), and the third group (9 mice, used as control) were i.p. injected with BPB at a dosage of 3 mg/kg, BPB at a dosage of 10 mg/kg, and phosphate buffered saline, respectively, 3 times per week from the 4th to 27th week of age. Urine glucose was monitored using Clinistix® (Bayer diagnostics, PA). Blood insulin and glucose were measured using the ELISA kit (Crystal Chem. Inc, IL) and a Glucometer Elite® (Bayer diagnostics, PA), respectively, at the 4th week, 15th week, and 18th week of age.

The results show that BPB significantly reduced the non-obese diabetic incidence. BPB also increased the blood insulin concentration and lowered the blood glucose concentration.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating a Th1-mediated disorder, comprising administering to a human subject in need thereof an effective amount of an isolated compound of formula I:

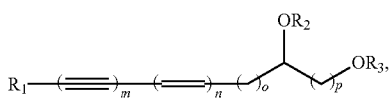

wherein
   $R_1$ is H, alkyl, aryl, or cyclyl;
   $R_2$ is pyranose;
   $R_3$ is H or alkyl;
   m is 2, 3, 4, 5, or 6;
   n is 0, 1, 2, or 3;
   o is 0, 1, 2, 3, 4;
   p is 1, 2, 3, or 4; and
   the Th1-mediated disorder is non-obese diabetes, Crohn's colitis, autoimmune hemolytic anemia, rheumatoid arthritis, autoimmune encephalitis, multiple sclerosis, or autoimmune myocarditis.

2. The method of claim 1, wherein m is 4 and n is 0.
3. The method of claim 2, wherein o is 2, and p is 1.
4. The method of claim 3, wherein $R_2$ is β-glucopyranose.
5. The method of claim 4, wherein $R_1$ is methyl and $R_3$ is H.
6. The method of claim 1, wherein $R_1$ is methyl, $R_2$ is β-glucopyranose, and $R_3$ is H.
7. The method of claim 6, wherein m is 4 and n is 0.
8. The method of claim 6, wherein m is 3, n is 1, o is 2, and p is 2.
9. The method of claim 6, wherein m is 3, n is 1, o is 2, and p is 1.
10. The method of claim 1, wherein m is 3, n is 1, o is 2, and p is 2.
11. The method of claim 1, wherein m is 3, n is 1, o is 2, and p is 1.
12. The method of claim 1, wherein the Th1-mediated disorder is non-obese diabetes.
13. A pharmaceutical composition, comprising a pharmaceutically acceptable carrier and a pure compound of formula I:

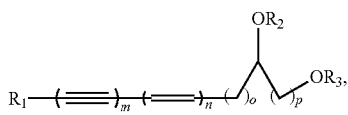

wherein
   $R_1$ is H, alkyl, aryl, or cyclyl;
   $R_2$ is pyranose;
   $R_3$ is H or alkyl;
   m is 2, 3, 4, 5, or 6;
   n is 0, 1, 2, or 3;
   o is 1, 2, 3, 4; and
   p is 1, 2, 3, or 4.

14. The composition of claim 13, wherein $R_1$ is methyl, $R_2$ is β-glucopyranose, and $R_3$ is H.
15. The composition of claim 14, wherein m is 4, n is 0, o is 2, and p is 1.
16. The composition of claim 15, wherein m is 3, n is 1, o is 2, and p is 2.
17. The composition of claim 16, wherein m is 3, n is 1, o is 2, and p is 1.

* * * * *